(12) United States Patent
Panjeton et al.

(10) Patent No.: US 12,318,599 B2
(45) Date of Patent: Jun. 3, 2025

(54) APPARATUS AND METHODS FOR BENDING A NEEDLE

(71) Applicants: UNIVERSITY OF FLORIDA RESEARCH FOUNDATION, INCORPORATED, Gainesville, FL (US); PANJCORP, LLC, Gainesville, FL (US)

(72) Inventors: Hess Amir Panjeton, Atlanta, GA (US); Geoffrey Danial Panjeton, Ballwin, MO (US)

(73) Assignees: UNIVERSITY OF FLORIDA RESEARCH FOUNDATION, INCORPORATED, Gainesville, FL (US); PANJCORP, LLC, Gainesville, FL (US)

( * ) Notice: Subject to any disclaimer, the term of this patent is extended or adjusted under 35 U.S.C. 154(b) by 157 days.

(21) Appl. No.: 17/787,501

(22) PCT Filed: Dec. 21, 2020

(86) PCT No.: PCT/US2020/066447
§ 371 (c)(1),
(2) Date: Jun. 20, 2022

(87) PCT Pub. No.: WO2021/127645
PCT Pub. Date: Jun. 24, 2021

(65) Prior Publication Data
US 2023/0034291 A1    Feb. 2, 2023

Related U.S. Application Data

(60) Provisional application No. 62/950,306, filed on Dec. 19, 2019.

(51) Int. Cl.
*B21D 7/02* (2006.01)
*A61M 5/32* (2006.01)
(Continued)

(52) U.S. Cl.
CPC ............. *A61M 5/329* (2013.01); *B21D 7/022* (2013.01); *B21F 1/06* (2013.01); *B21G 1/08* (2013.01); *A61M 2207/10* (2013.01)

(58) Field of Classification Search
CPC ....................................................... B21F 1/06
See application file for complete search history.

(56) References Cited

U.S. PATENT DOCUMENTS

| 2,346,371 | A | 4/1944 | Fink |
| 2,455,138 | A | 11/1948 | Perkins |
(Continued)

FOREIGN PATENT DOCUMENTS

| CN | 203155878 | 8/2013 |
| CN | 204953745 U | * 1/2016 |
(Continued)

OTHER PUBLICATIONS

Machine translation of CN 204953745 (Year: 2016).*
(Continued)

*Primary Examiner* — Debra M Sullivan
(74) *Attorney, Agent, or Firm* — Timothy H. Van Dyke; Wolter Van Dyke Davis, PLLC

(57) ABSTRACT

Methods and devices for bending a needle are provided. A device embodiment can include a needle bending apparatus for imparting a bend in a needle when a needle is received therein. The needle bending apparatus may include a housing having an aperture for receiving a shaft of a needle; and at least one abutment member comprising a needle interfacing surface for supporting a portion of the needle and providing a surface upon which the needle may be bent.

3 Claims, 12 Drawing Sheets

(51) Int. Cl.
  B21D 7/022  (2006.01)
  B21F 1/06  (2006.01)
  B21G 1/08  (2006.01)

(56) References Cited

U.S. PATENT DOCUMENTS

| | | | |
|---|---|---|---|
| 3,433,042 | A | 3/1969 | Crihfield et al. |
| 3,464,247 | A | 9/1969 | Beckwell |
| 5,201,210 | A | 4/1993 | Stein, III |
| 5,425,258 | A | 6/1995 | Bogart |
| 5,819,571 | A * | 10/1998 | Johnson ............ A61F 9/00745 72/31.12 |
| 9,138,224 | B2 | 9/2015 | Matsutani et al. |
| 9,415,171 | B2 | 8/2016 | Peterson |
| 2004/0210245 | A1 | 10/2004 | Erickson et al. |
| 2008/0087065 | A1 | 4/2008 | Hainzinger |
| 2010/0263425 | A1 | 10/2010 | Matsutani et al. |

FOREIGN PATENT DOCUMENTS

| | | |
|---|---|---|
| EP | 3005953 | 8/2007 |
| WO | 2021127645 | 6/2021 |

OTHER PUBLICATIONS

PCT/US2020/066447, PCT search report & written opinion, mailed date Apr. 2, 2021, 14 pages.
Abidin, Michael R. et al., "Biomechanics of curved surgical needle bending", Journal of Biomedical Materials Research, 1989, vol. 23, issue S13, pp. 129-143.
Panjeton, Geoffrey D. et al., "Survey of Interventional Pain Physicians on Bending Spinal Needles for Chronic Pain Procedures", Interventional Pain Management Reports, 2020, vol. 4, No. 1, pp. 5-8.
Sitzman, B. Todd et al., "The Effects of Needle Type, Gauge, and Tip Bend on Spinal Needle Deflection", Regional Anesthesia ans Pain Management, 1996, Anesth Analg, vol. 82, pp. 297-301.
SybronEndo Needle Bending Tool, Vendor: net32.com, Dental Supply Marketplace, https://www.net32.com/ec/sybronendo-needle-bending-tool-d-137853, downloaded from Internet Jun. 5, 2022, 2 pages.
ESSR, EP 20901616.1, mailed Nov. 17, 2023, 7 pages.

* cited by examiner

APPARATUS AND METHODS FOR BENDING A NEEDLE

CROSS REFERENCE TO RELATED APPLICATIONS

This application claims priority to U.S. Provisional Patent Application No. 62/950,306, filed Dec. 19, 2019, titled APPARATUS AND METHODS FOR BENDING A NEEDLE, which is incorporated by reference herein.

BACKGROUND

Studies have shown that between 54% and 80% of the population will experience spinal pain at some point throughout their lifetime. A common method for treating spinal or spinal-related pain is to prescribe an opioid medication. Unfortunately, this often requires increasing dosages of the medication to achieve pain relief, which has been known to cause opioid addiction.

In recent years, alternative treatments have been developed for diagnosing and treating spinal and other types of chronic pain based on anatomic etiologies. Interventional procedures such as nerve root blocks, radiofrequency ablation, and joint injections have been used to block pain directly at the source. These procedures utilize fluoroscopic imagery techniques to guide one or more needles inserted through tissues to reach nerves, sometimes located between facets or joints in the spine. A limiting factor in these procedures can be the ability to reach a target tissue. Missing the target tissue by even a few millimeters can result in incomplete or failed treatment. Complications due to needle placement can cause further damage and additional pain.

Typical needles used for procedures in and around the spine are straight 22 gauge or 25 gauge hypodermic needles about 2 to 7 inches in length. In order to facilitate insertion into certain areas, such as between facets in the spine, surgeons will often manually bend the sharp end of the needle to impart a bend or curvature. For obvious reasons, this manual needle bending can be dangerous to the surgeon and can result in skin punctures, contamination of the needle, and variability in the bend or curvature that can make it difficult to maneuver. Commercially available products with pre-bent tips are available in a limited number of curvatures, usually about 10° to 15° or less; however, these pre-set pre-bent tips may not be suitable for all situations.

The variability between patients and the precision necessary to perform pain blocking procedures usually necessitates that needles be customized to different curvatures. There is a need for a device that can be used during a procedure to bend needles to any specific degree, as required for individual patients. Preferably, such a device would be easy to use, provide a consistent, smooth, regular bend to the needle, and avoid constriction of the lumen.

SUMMARY

The embodiments described herein provide devices and methods that address the problem of bending hypodermic spinal needles to varying degrees, while achieving consistency in the bending and maintaining safety of the user. In one embodiment, the subject invention provides a manually-operated needle bending apparatus. The needle-bending apparatus embodiments of the subject invention address the above described disadvantages associated with manually bending needles and provide attributes and advantages over commercially available pre-bent needles. In particular, the needle-bending apparatus of the subject invention can be used to bend spinal needles to any degree necessary for a particular need or patient and does not require direct contact by the operator with the needle tip during the bending process.

In one embodiment, a needle-bending apparatus embodiment has a base with a sloped face and needle slot that leads to a groove with a port for receiving a spinal needle. A presser with a sloped face may be associated with the base, and can be rotatably attached to the base so that it rotates bringing the second face of the base closer to, or in proximity with, the sloped face on the presser. A spinal needle may be placed in the groove such that its needle tip extends out of the groove to project over the sloped face. When the presser is rotated, the sharp end of the spinal needle contacts the second face. Continued advancement of the presser forces the needle to bend at or about where it exits the port, so that the sharp end is forced toward the second face on the base until it has a desired bend. Advantageously, the sloped face provides support to the length of the needle being bent, which can inhibit breakage. Moreover, the location on the needle at which the bend occurs can be positioned at any point along the needle shaft, and can be adjusted as needed based on the use for the bent needle by varying the depth of the position of the needle within the slot.

In another embodiment, a needle bending apparatus, comprising a housing having an aperture for receiving a distal portion of a needle, and at least one abutment member comprising a needle interfacing surface for supporting a portion of the needle is provided, the apparatus providing a surface upon which the needle may be bent. The apparatus may further include grooves or protuberances as demarcations for measuring the angle of bend of the needle, and for causing the angle bend of the needle, in some embodiments.

The apparatus embodiments described herein are easy to manipulate when wearing surgical gloves, and provide a surgeon the ability to use experience and current knowledge of the patient to form the necessary angle in a spinal needle for immediate use. These apparatuses are capable of being sterilized, or may alternatively be made for sterile use with one patient and subsequently disposed. Use of a needle-bending embodiment can eliminate the unsafe and imprecise practice of bending spinal needles by hand, and can provide accurate angular positioning of the needle, while providing easily customizable needles to accommodate different patient anatomies and various procedures.

BRIEF DESCRIPTION OF DRAWINGS

In order that a more precise understanding of the above recited invention can be obtained, a more particular description of the invention briefly described above will be rendered by reference to specific embodiments thereof that are illustrated in the appended drawings. The drawings presented herein may not be drawn to scale and any reference to dimensions in the drawings or the following description is specific to the embodiments disclosed. Any variation of these dimensions that will allow the subject invention to function for its intended purpose are considered to be within the scope of the subject invention.

DETAILED DESCRIPTION

Figure 1:
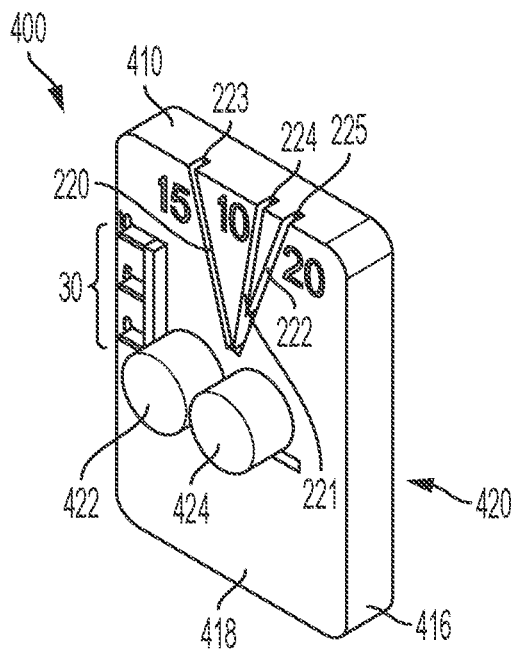
FIG. 1 shows a perspective view of an embodiment of a needle-bending apparatus.

The subject invention provides an apparatus that can be utilized to bend needles for a surgical procedure. More specifically, the subject invention provides a needle-bending apparatus for use in bending needles. In one example, the needle to be bent may include a hypodermic spinal needle. The embodiments described herein provide a safe, accurate, consistent, and immediate method for bending spinal needles resulting in a standardized needle shape and curve and decreasing risk to the operator. Advantageously, needles can be bent to any of a variety of angles using the needle-bending apparatus, such that needles can be customized to the needs of individual patients. The embodiments described herein can reduce or eliminate variability of bent needles between operators or within the same operator resulting in a standardized bending process to provide consistent results.

The subject invention is particularly useful in the field of diagnostic and interventional procedures. In particular, the needle-bending apparatus disclosed herein are useful in procedures for administering pain relieving medicaments to spinal nerves using hypodermic spinal needles. This does not preclude the embodiments herein being utilized with other types of needles that may be useful for other types of procedures. Certainly there is a benefit in providing a standardized bend in a needle, for example, wherein the bend occurs in generally the same distance from the tip of the needle on all needles of the same size and/or gauge, or for example, consistency in the angle of the bend, at least across needles of the same gauge, for example. Consistency and standardization reduces the element of surprise, which is beneficial in a surgical procedure wherein the needle is inserted into a patient. Patients anatomically can differ, resulting in variables that must be addressed by the operator or physician treating the patient, and therefore, providing a device that can bend a needle in a particular position on the needle shaft and at a particular angle provides a safer environment for a procedure.

In the description that follows, a number of terms related to spinal surgery and needles used therefore are utilized. In order to provide a clear and consistent understanding of the specification and claims, including the scope to be given such terms, the following definitions are provided.

The term "patient" as used herein, describes an animal, including mammals, to which the apparatus and methods of the present invention can be applied and that can benefit from such application. This can include mammalian species such as, but not limited to, apes, chimpanzees, orangutans, humans, and monkeys; domesticated animals (e.g., pets) such as dogs, cats, guinea pigs, and hamsters; veterinary uses for large animals such as cattle, horses, goats, and sheep; and, any wild or non-domesticated animal.

The term "surgeon" as used in the subject invention is merely for literary convenience.

The apparatuses, methods, techniques and/or procedures of the subject invention can be utilized by any person desiring or needing to do so and having the necessary skill and understanding of the invention.

Further, the term "needle" as used herein refers to any surgical or hypodermic needle for injection or insertion into tissue. This can include suture needles and hypodermic needles, such as spinal injection needles, as well as other needles capable of being bent with embodiments of the apparatus of the subject invention. By way of example, hypodermic needles specific for administering treatment in and around the spinal area are usually about 22 gauge or 25 gauge and between 2" and 7" in length. Such needles can be used with embodiments of the subject invention.

Unless otherwise specifically stated, the terms "operable communication," "operable connection," "operably connected," "cooperatively engaged" and grammatical variations thereof mean that the particular elements are connected in such a way that they cooperate to achieve their intended function or functions. The "connection" or "engagement" may be direct, or indirect, physical or remote.

It is to be understood that the figures and descriptions of embodiments of the present invention have been simplified to illustrate elements that are relevant for a clear understanding of the invention, while eliminating, for purposes of Clarity, other elements that may be well known.

Finally, reference is made throughout the application to the "front end" and "rear end." As used herein, the front end is that end at which a needle is placed and towards which the presser advances to bend a needle. For example, the presser closes over the front end of the base. Conversely, the rear end is that end at which the presser operably connects with the base. For example, the presser opens towards the rear end of the needle-bending apparatus, in one embodiment. The embodiments are more particularly described in the following examples that are intended to be illustrative only because numerous modifications and variations therein will be apparent to those skilled in the art. As used in the specification and in the claims, the singular for "a," "an" and "the" include plural referents unless the context clearly dictates otherwise.

A study was conducted on the variability of spinal needle manipulation among interventional pain proceduralists, the results of which further demonstrate the need for the embodiments described herein. Despite the high reported prevalence of spinal needle bending (74%) among interventional pain proceduralists (1), there is a paucity of literature providing guidance on this aspect of procedural technique. One study investigated the effect of 0°, 5°, and 10° of needle bend on trajectory deflection (2). There is limited published literature that suggests this range of bend is currently utilized by interventional pain proceduralists in practice.

The objectives of this study were to measure variation in the degree and inflection point of spinal needle bending, comparing intra- and inter-subject variability as well as comparing attendings to fellows in training. This study also aims to determine a baseline for the current practice. Reference will be made to the attached Figures on which the same reference numerals are used throughout to indicate the same or similar components. With reference to the attached Figures, which show certain embodiments of the subject invention, it can be seen that the subject invention comprises a needle-bending apparatus FIGS. 1-5 provide an embodiment of a needle bending apparatus 400 including a first and a second abutment member 422, 424, for abutting and supporting a shaft of the needle 15 to allow for bending of the needle 15. The abutment members 422, 424 are formed as protrusions which extend from the surface of the apparatus 400. Examples of various bending angles are shown in FIGS. 1-5, including a 10, 15, and 20 degree bending angle. The angle guide grooves 220, 221, 222 can be used to guide the bend of the needle during use of the apparatus 400. In one embodiment, grooves 220, 221, 222 may be provided for angle demarcations; however, in another embodiment, these angle demarcations may include raised protuberances. These raised protuberances may abut a needle to allow bending of the needle to the desired angle marked by the raised protuberance, wherein the protuberance may provide a surface against which to apply pressure to the needle to create the bend in the needle of the desired angle. The protuberances and grooves 220, 221, 222 may also be used to measure the angle of the bend of a bent needle. In yet another embodiment, no raised protuberances or grooves may be provided, and the surface of the apparatus may be marked with a visual guide for aligning the needle to effect a particular angular bend in the needle. The embodiments described herein may further include an apparatus with any combination of grooves, protuberances and/or visual guides to aid in aligning the needle for bending. In some embodiments of the apparatus described herein, use of a turn in a needle slot for receiving the needle during its bending can help contain the needle if it breaks, so that the pieces can be retained in the needle slot.

Figure 2:
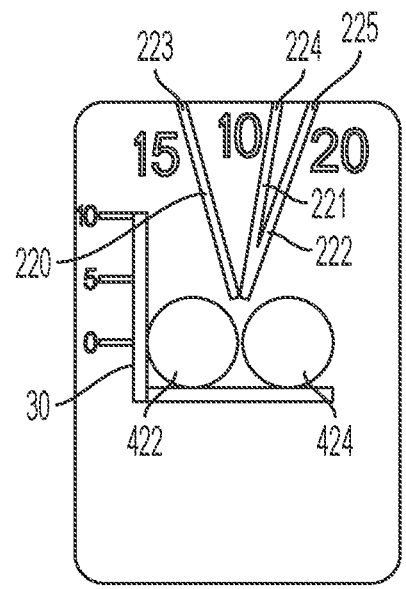
FIG. 2 shows a front side view of an embodiment of a needle-bending apparatus shown in FIG. 1.
Figure 3:
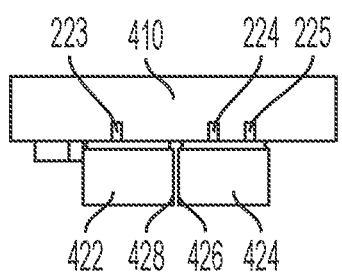
FIG. 3 shows a top end view of an embodiment of a needle bending apparatus shown in FIG. 1.
Figure 4:
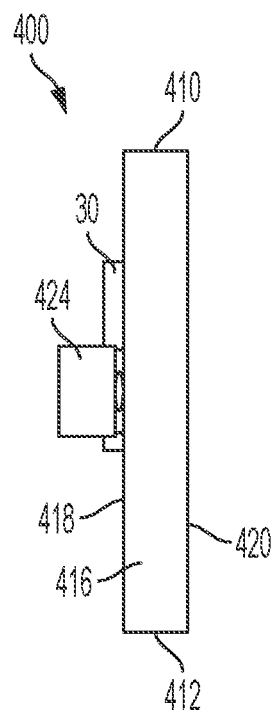
FIG. 4 shows a side view of an embodiment of a needle bending apparatus shown in FIG. 1.
Figure 5:
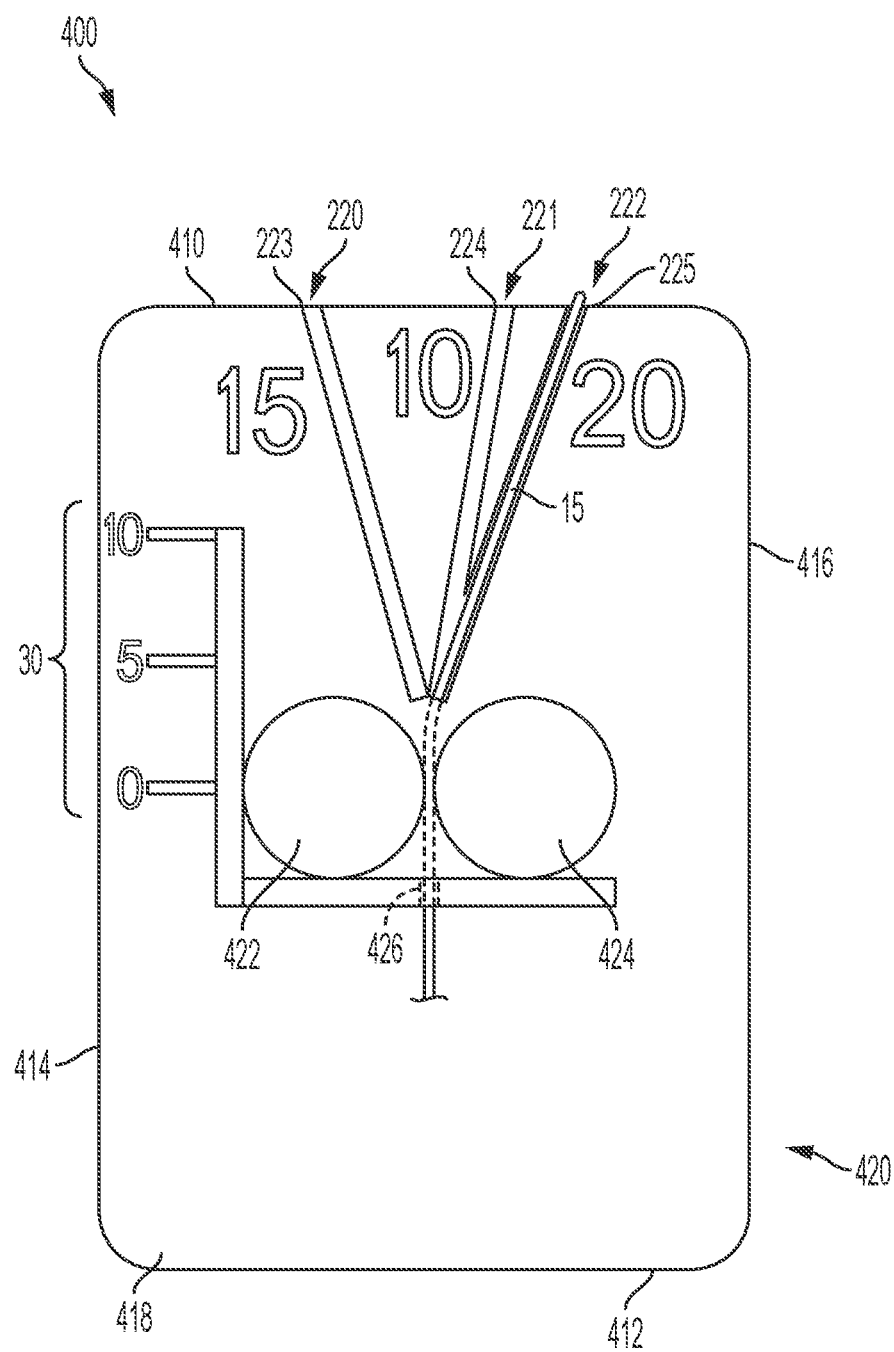
FIG. 5 shows a front side view of an embodiment of a needle bending apparatus as shown in FIG. 1, in use, with a needle received therein, the needle being bent to a 20-degree angle.
Figure 6:
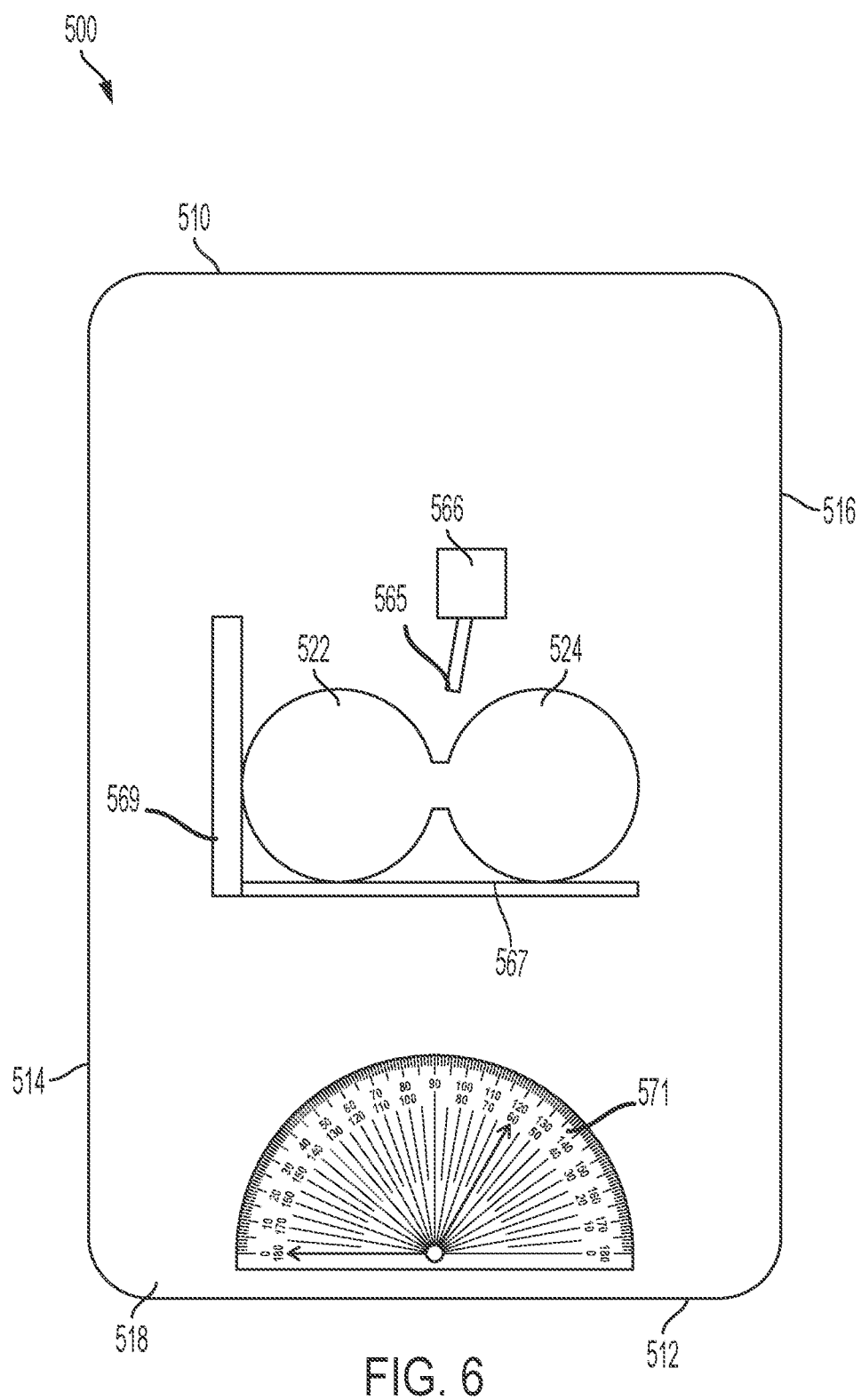
FIG. 6 is a front side view of another embodiment of a needle bending apparatus.
Figure 7:
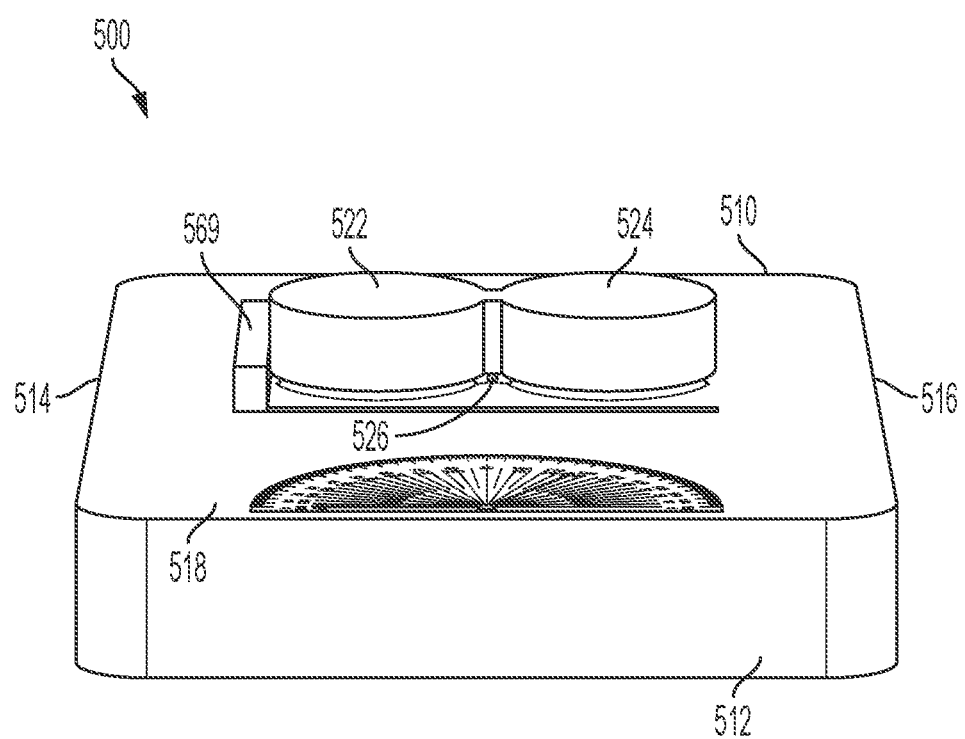
FIG. 7 is a bottom side view of the embodiment of the needle bending apparatus shown in FIG. 6.
Figure 8:
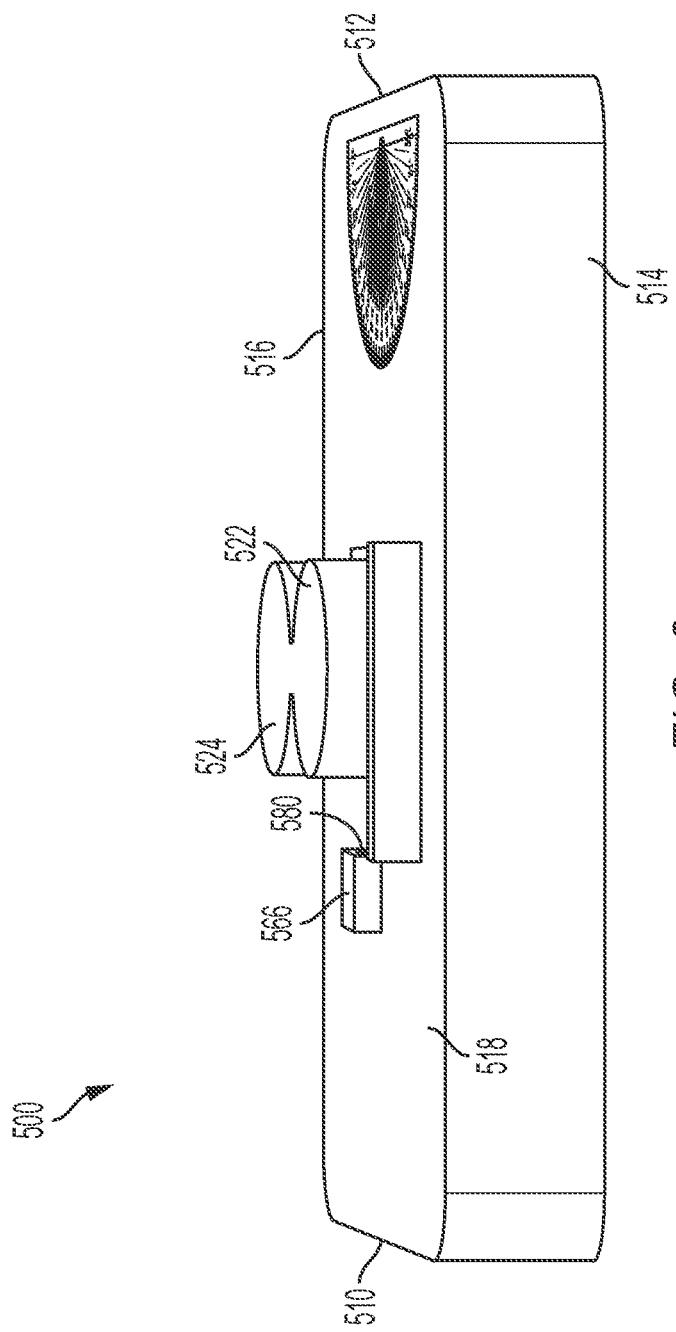
FIG. 8 is a side perspective view of the embodiment of the needle bending apparatus shown in FIG. 6.
Figure 9:
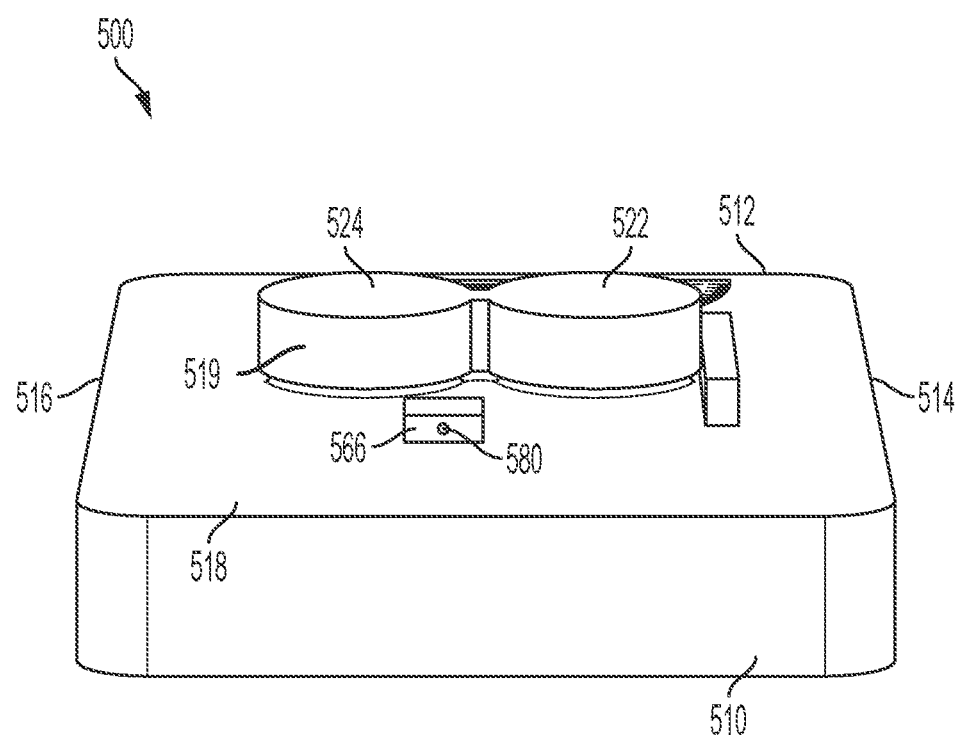
FIG. 9 is a top side view of the embodiment of the needle bending apparatus shown in FIG. 6.
Figure 10:
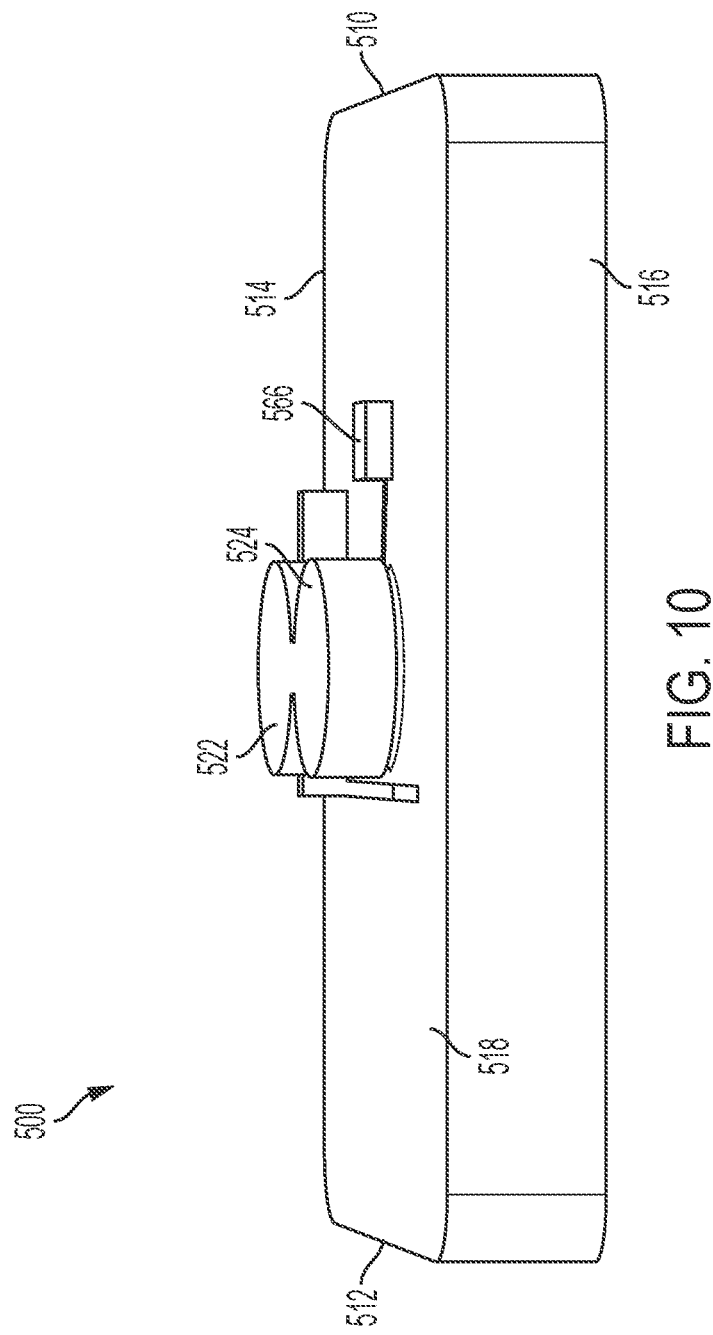
FIG. 10 is a side perspective view of the embodiment of the needle bending apparatus shown in FIG. 6.

FIG. 1 shows a perspective view of the embodiment of a needle-bending apparatus 400 shown in FIGS. 1-5 wherein the apparatus 400 includes a top side 410, bottom side 412, first side 414, and second side 416. The apparatus 400 further includes a front side 418 and a back side 420. The apparatus 400 may be formed of any shape, including but not limited to a square, cylinder, spherical shaped apparatus. FIGS. 1, 2 and 5 provide a view of a scale 30 for providing a reference of size or length of the portion of the needle 15 on which the bending is occurring during use of the apparatus 400. The scale may be provided as an extrusion from the apparatus 400, serving as a 10 mm scale to allow users to form the bend at a predetermined distance from the needle tip. An example of a needle 15 being deformed by the apparatus 400 is shown in FIG. 5, wherein the needle 15 is deformed, or bent at a 20-degree angle in FIG. 5 using 20 degree angle guide groove 222. FIG. 7 shows a front side view of the apparatus embodiment 400 as shown in FIG. 6 showing the 15 degree, 10 degree, and 20 degree angle guide grooves, 220, 221, 222, respectively, shown as non-limiting embodiments of positions for placement of a needle during bending of the needle using the apparatus described herein. Angle tip ports 223, 224, and 225, for the 15, 10, and 20 degree angle guide grooves, respectively, are shown in FIG. 2. The angle tip ports 223, 224, and 225 are also shown in the top side view of the apparatus 400 in FIG. 3. FIG. 3 also an aperture 426 for receiving and stabilizing a needle 15 during use of the apparatus 400, wherein in positioning the needle 15 in the apparatus for use, the needle is passed through the port 426 as shown in FIG. 5, between abutment members 422, 424, and into one of the angle guide grooves 220, 221, 222, for example. Pressure may then be applied to the needle 15 to bend the needle against one of the abutment members 422, 424. FIG. 3 further shows a space 428 between first and second abutment members 422, 424. FIG. 4 shows a side view of an embodiment of a needle bending apparatus 400 shown in FIG. 1.

The needle bending apparatus can be held in one or both hands to form a bend in a needle 15. Either configuration provides the advantage of being able to control the amount of bend or angle imparted to the sharp end 16 of a needle 15.

The bend imparted to the needle 15 may be applied toward the needle tip or proximal end of the needle, in non-limiting embodiments, as customized or adjusted by a surgeon to meet the specific needs of a patient. In one embodiment, the needle bending apparatus is sterilized and/or sterilizable, for utilization in an operating environment.

As force is applied to the needle 15 front end 10 to impart a bend, stresses can be applied along the length of the needle 15. Needles typically have limited flexural rigidity. Thus, while they are stiff, it still possible for them to bend and deform along their length, particularly during use. This characteristic allows needles to be bent utilizing the devices of the subject invention. When a needle breaks, the stored potential energy can translate into kinetic energy. If the needle is not contained when it breaks, the broken end(s) can become potential projectiles due to release of the stored potential energy in the needle shaft.

In one embodiment, the needle bending apparatus has one or more rulers, degree scales, graduated marks, or other types of indicia, or indicator, 569, 571 that can measure the length along the shaft of the needle 15 at which the needle bend is applied. These rulers, degree scales, graduated marks, or other indicators 569, 571 may be provided as extrusions from the apparatus 400, 420, 500, grooves into the apparatus 400, 420, 500, or visual markers flush with the surface of the apparatus 400, 420, 500 as shown in FIG. 6-11.

In the embodiments described herein, a needle 15 may bend in response to the force (F) applied by a user. In at least one embodiment, the surface of the apparatus may be smooth or polished to facilitate sliding and inhibit damage or breakage to the needle 15. In another embodiment, surface may include a low-coefficient-friction material. For example, the sloped face can be chrome-plated, polytetrafluoroethylene (PTFE), plastic, nylon, graphite, diamond-like-material (DLC), any of various ceramics, metals and combinations thereof. In a particular embodiment, the surface can be a removable cover.

The angle of the sloped face can vary depending upon the range of bend angles to be made on a needle 15. In one embodiment, the angle of the sloped face, relative to the front end, is between approximately 60° and approximately 25°. In a more particular embodiment, the angle of the sloped face, relative to the front end is between approximately 50° and approximately 30°. In a specific embodiment, the angle of the sloped face, relative to the front end, is approximately 45°.

The apparatus embodiments described herein may be provided as disposable apparatuses, for example, or may be reusable. In one embodiment, the apparatus may be sterilized following use and thereafter available for a subsequent use.

The administration of treatments and medicaments in the body can require precise placement of a needle. Oftentimes, the most effective way to reach difficult areas of the body, particularly between or within vertebrae is to use a bent or curved needle. The subject embodiments described herein provides an apparatus that can allow a surgeon to form a bent needle before or during a procedure. This allows the needle to be bent to a customized angle specific to the needs of a patient. The apparatus embodiments described herein provide an easy and safe alternative to the current practice of bending needles by hand.

FIGS. 6-10 include various views of yet another embodiment of a needle bending apparatus 500 including a top side 510, bottom side 512, first side 514, and second side 516. The apparatus 500 further includes a front side 518 and a back side 520 and a protrusion 566. The apparatus 500 may be formed of any shape, including but not limited to a square, cylinder, spherical shaped apparatus. A first and a second abutment member 522, 524, for abutting and supporting a shaft of the needle to allow for bending of the needle. The abutment members 522, 524 are formed as protrusions which extend from the surface of the apparatus 400. An aperture 526 is formed in the apparatus to allow a needle to pass through the aperture 526, extend between the abutment members 522, 524, and contact the protrusion 566. The protrusion 566 may be positioned onto the needle interfacing surface 519 of either one of the abutment members 522, 524 such that when a needle is placed between the abutment members 522, 524 and in contact with the protrusion 566, an angle of between 5-15 degrees may be imparted on the needle. The protrusion may also include an aperture 580 into which the needle can be inserted. In a more particular example, an angle of 10 degrees may be imparted on the needle. The needle may be bent either direction, toward the first or second abutment member 422, 522, or 424, 524, respectively, to impart the bend in the needle. Direction may be based on the comfort of the user.

A notch 565 is provided adjacent to the protrusion 566 to receive a tip of the needle and limit contact between the user and the needle tip during bending of the needle, in one non-limiting embodiment. One or more grooves 567 may be provided to indicate entry direction for the needle. A measurement scale 569 may be provided adjacent to the abutment members 522, 524 to approximate distance from the needle tip for the bend of the needle, allowing a user to adjust the positioning and location for the needle bend during use of the apparatus 500. Rulers, degree scales, graduated marks, or other indicators 571 may be provided on the apparatus 400, 500 (as shown in FIGS. 6-10) to measure various details relating to the needle, including, but not limited to, the angle of the bend of the needle, the length of the needle, the distance between the proximal or distal end of the needle and the position of the bend in the needle, among other measurements. A similar ruler, degree scale, graduated mark, or other indicator 571 may be provided in the embodiment of the apparatus 400, though not shown in the FIGS.

EXAMPLES

Methods

In this observational prospective cohort study 4 fellows in the Multidisciplinary Pain Fellowship Program and 4 attending physicians in the Division of Pain Medicine at the University of Florida were provided twenty 22G and 25G 3.5" spinal needles in a randomly generated order following informed consent. They were instructed to bend the needle as they typically would for lumbar medial branch block injections. Thereafter, standardized images of the needles were captured ensuring for spatial calibration and measurements were taken using ImageJ in triplicate for the following metrics: distance from initiation of bend to needle point, angle of bend, length of bent portion of needle, and length of deformation. Data were analyzed in SAS proc mixed, SAS 9.4.

The study demonstrated that the average bend angle was 14.01° for 22G needles and 13.84° for 25G needles. The average distance from the needle tip to the bend was 0.9 cm for 22G needles and 0.8 cm for 25G needles. Amongst 22G needles, there was about twice as much variation within one subject's needles as compared to variation between subjects. Measurement error in all cases was negligible compared to the variability both within subjects and between subjects.

The results of this study demonstrated the significant variability in the practice of needle bending. Until this point, very limited investigation has occurred on this commonly utilized manual needle-bending technique. The results of this study provide support for the inventive embodiments described herein to optimize spinal needle manipulation for various procedures, including interventional pain procedures.

Results

1. Summary Statistics

TABLE 1

| Variable | N | Mean | StdDev | Coeff of Variation |
|---|---|---|---|---|
| type = 22G | | | | |
| length | 80 | 8.87 | 0.25 | 2.82 |
| tip | 80 | 0.90 | 0.19 | 20.59 |
| deform | 80 | 0.30 | 0.07 | 24.62 |
| bend | 80 | 1.00 | 0.19 | 18.68 |
| angle | 80 | 14.01 | 3.38 | 24.13 |
| type = 25G | | | | |
| length | 80 | 8.66 | 0.08 | 0.94 |
| tip | 80 | 0.80 | 0.23 | 28.37 |
| deform | 80 | 0.24 | 0.07 | 30.23 |
| bend | 80 | 0.89 | 0.23 | 25.83 |
| angle | 80 | 13.84 | 3.53 | 25.51 |

2. Variance Components:

Measurement error is estimated by the residual; in all cases it is very small (approximately 10 times smaller than variability resulting from subject differences and within subject variability). So measurement error is negligible compared to the variability both within subjects and between subjects.

Figure 15:
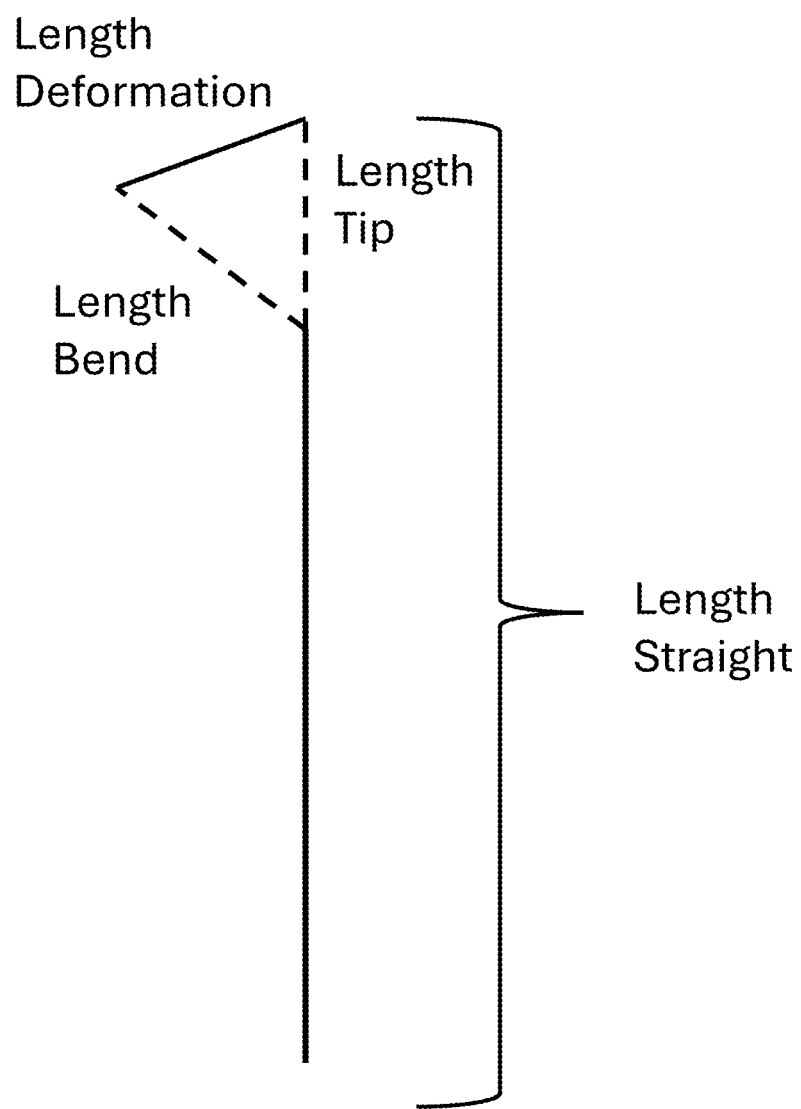
FIG. 15 is a diagram that illustrates length of bend and angle, length of deformation and length tip.

For tip 22 ga, within-subject variability is dominant—individual variation is approx. twice as much as variations between subjects (individuals not consistent). For 25 ga tip, the variation is about the same within and between individuals. Similar patterns for bend and deform were observed. The diagram in FIG. 15 illustrates length of bend and angle, length of deformation and length tip.

Note that for the angle of bend, between-subject variability is largest, individuals differ more than the variation within each subject. The dotplots bear this out—subject A_D tend to prefer larger angles, the others more shallow angles. Average angle was approx. 14 degrees—much more than tested by Sitzamn and Uncles, Anesth Analg 1996; 82:297-301

TABLE 2

| | LENGTH | | TIP | |
|---|---|---|---|---|
| 22 ga | Covariance Estimates | Parameter | Covariance Estimates | Parameter |
| | Cov Parm | Estimate | Cov Parm | Estimate |
| | subject | 0.05895 | subject | 0.01205 |
| | needle(subject) | 0.009682 | needle(subject) | 0.0222 |
| | Residual | 0.001815 | Residual | 0.005383 |
| 25 ga | Covariance Estimates | Parameter | Covariance Estimates | Parameter |
| | Cov Parm | Estimate | Cov Parm | Estimate |
| | subject | 0.000666 | subject | 0.0277 |
| | needle(subject) | 0.005506 | needle(subject) | 0.02593 |
| | Residual | 0.001495 | Residual | 0.00268 |

TABLE 3

| | DEFORM | | BEND | |
|---|---|---|---|---|
| 22 ga | Covariance Estimates | Parameter | Covariance Estimates | Parameter |
| | Cov Parm | Estimate | Cov Parm | Estimate |
| | subject | 0.000198 | subject | 0.009666 |
| | needle(subject) | 0.00521 | needle(subject) | 0.02543 |
| | Residual | 0.000676 | Residual | 0.003304 |
| 25 ga | Covariance Estimates | Parameter | Covariance Estimates | Parameter |
| | Cov Parm | Estimate | Cov Parm | Estimate |
| | subject | 0.00189 | subject | 0.02875 |
| | needle(subject) | 0.003551 | needle(subject) | 0.02616 |
| | Residual | 0.000605 | Residual | 0.001905 |
| | ANGLE | | | |
| 22 ga | Covariance Estimates | Parameter | | |
| | Cov Parm | Estimate | | |
| | subject | 6.8448 | | |
| | needle(subject) | 5.0307 | | |
| | Residual | 0.9981 | | |
| 25 ga | Covariance Estimates | Parameter | | |
| | Cov Parm | Estimate | | |
| | subject | 7.646 | | |
| | needle(subject) | 5.3722 | | |
| | Residual | 0.9363 | | |

FIGS. 11-14 provide Dot plots of subject variability in tip length (mm), linear deformation (mm), bend (mm), and angle of bend (degrees).

Figure 11:
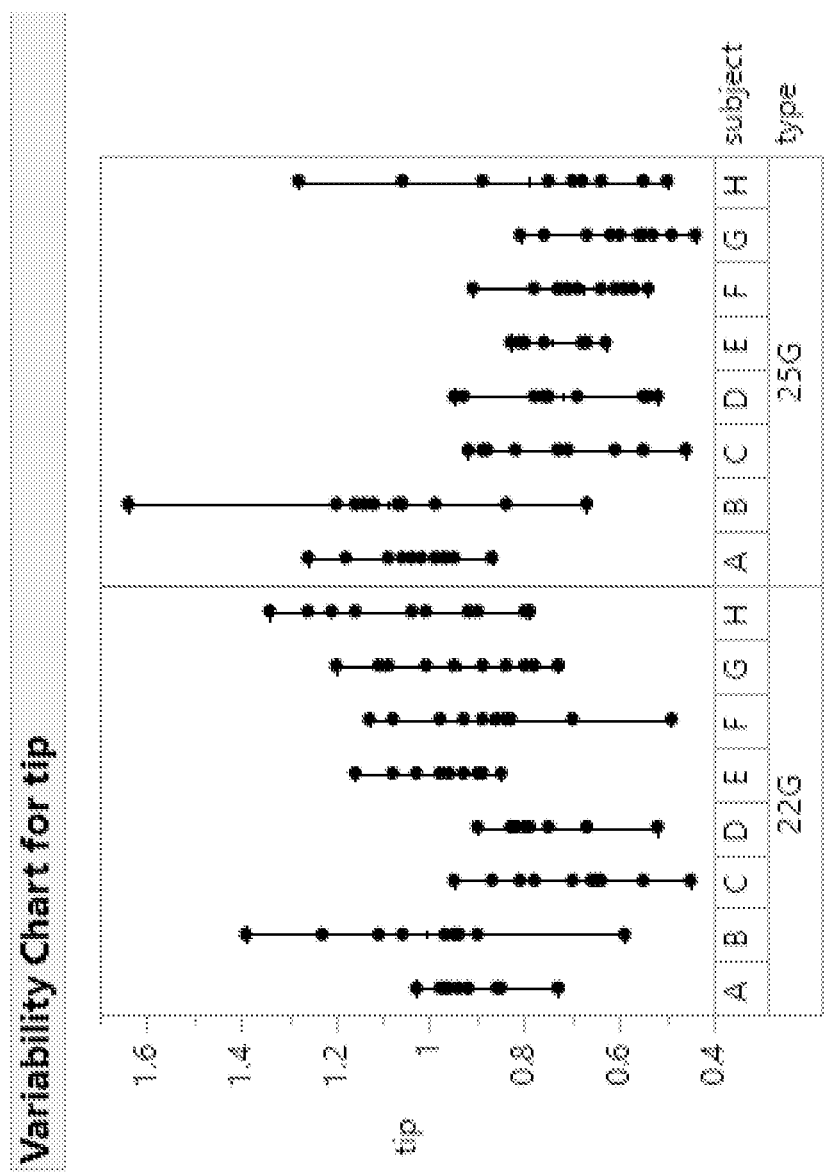
FIG. 11 shows a chart of tip length variability from a study performed by the inventors analyzing variability in manually bending 20 spinal needles (ten 22-gauge and ten 25-gauge per participant). The x-axis illustrates the participants (A-H) and is divided into 22-gauge and 25-gauge needle sizes. The y-axis illustrates the variability in distance from the needle tip (cm) at which the bend was applied.

FIG. 11 shows a chart of tip length variability from a study performed by the inventors analyzing variability in manually bending 20 spinal needles (ten 22-gauge and ten 25-gauge per participant). The x-axis illustrates the participants (A-H) and is divided into 22-gauge and 25-gauge needle sizes. The y-axis illustrates the variability in distance from the needle tip (cm) at which the bend was applied.

Figure 12:
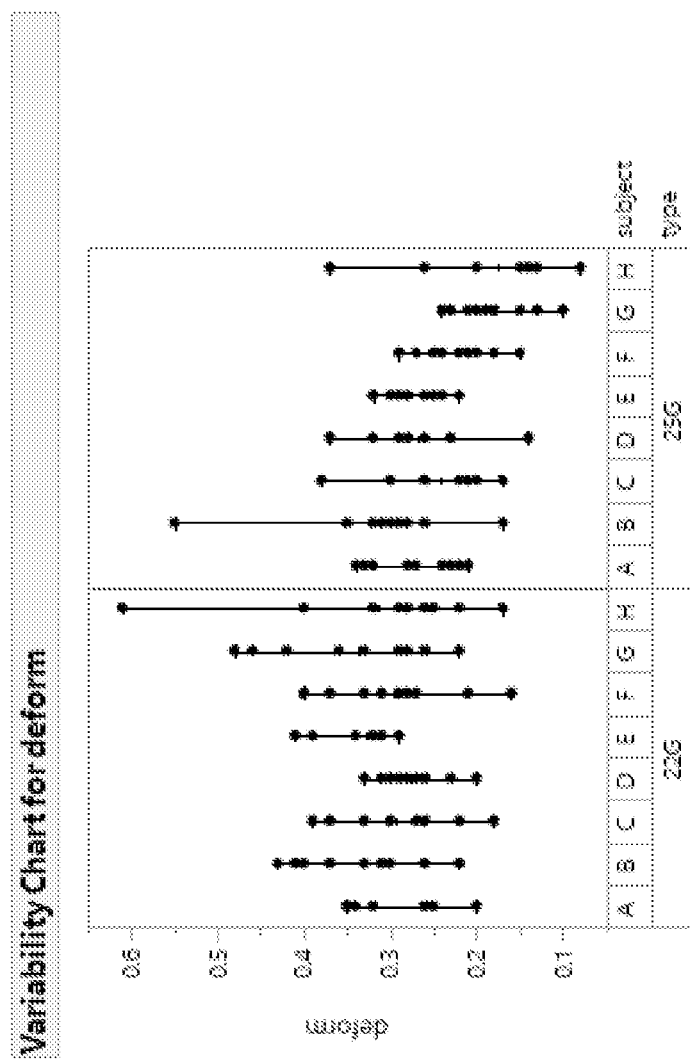
FIG. 12 shows a chart of length of deformation from a study performed by the inventors analyzing variability in manually bending 20 spinal needles (ten 22-gauge and ten 25-gauge per participant). The x-axis illustrates the participants (A-H) and is divided into 22-gauge and 25-gauge needle sizes. The y-axis illustrates the variability in the length of needle deformation (cm) from neutral applied to the needle tip.

FIG. 12 shows a chart of length of deformation from a study performed by the inventors analyzing variability in manually bending 20 spinal needles (ten 22-gauge and ten 25-gauge per participant). The x-axis illustrates the participants (A-H) and is divided into 22-gauge and 25-gauge needle sizes. The y-axis illustrates the variability in the length of needle deformation (cm) from neutral applied to the needle tip.

Figure 13:
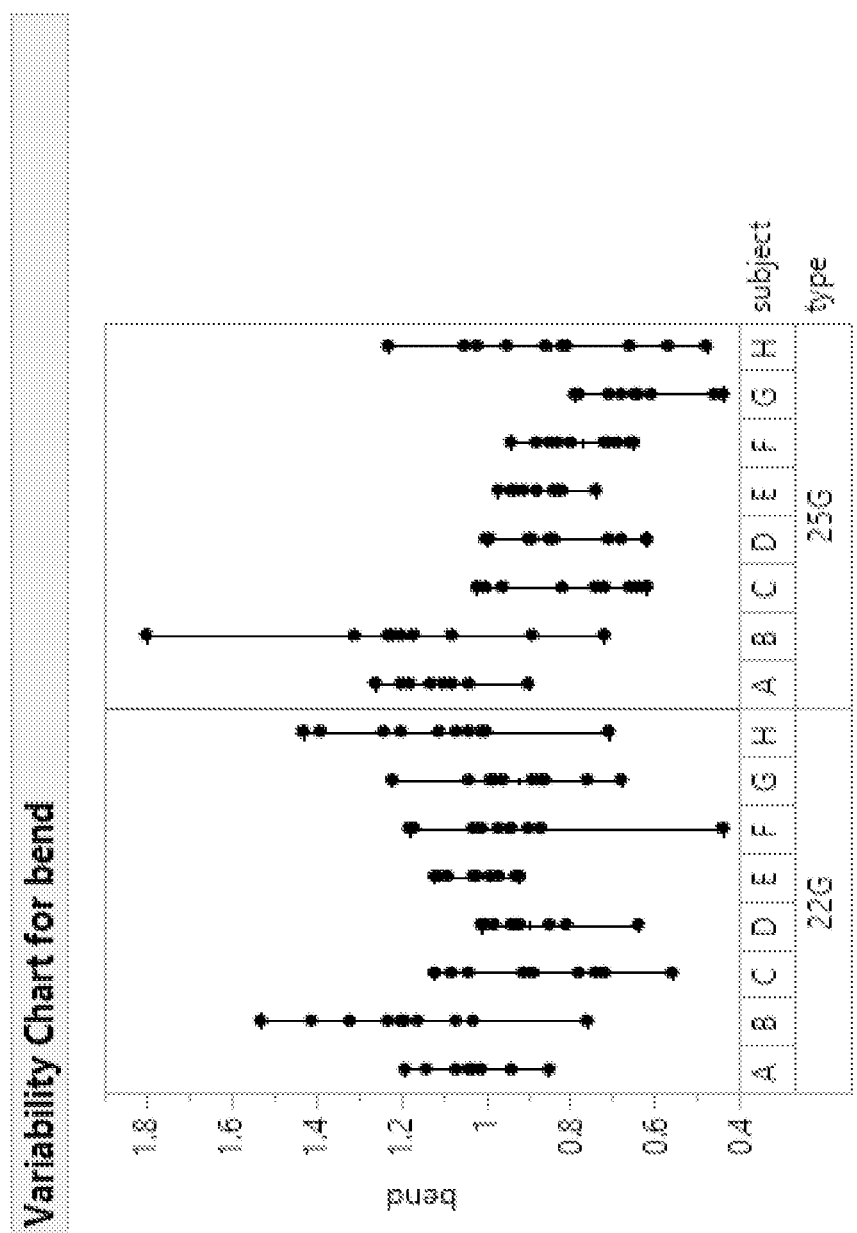
FIG. 13 shows a chart of length of bend from a study performed by the inventors analyzing variability in manually bending 20 spinal needles (ten 22-gauge and ten 25-gauge per participant). The x-axis illustrates the participants (A-H) and is divided into 22-gauge and 25-gauge needle sizes. The y-axis illustrates the variability in the length of needle bend (cm) from the needle tip.

FIG. 13 shows a chart of length of bend from a study performed by the inventors analyzing variability in manually bending 20 spinal needles (ten 22-gauge and ten 25-gauge per participant). The x-axis illustrates the participants (A-H) and is divided into 22-gauge and 25-gauge needle sizes. The y-axis illustrates the variability in the length of needle bend (cm) from the needle tip.

Figure 14:
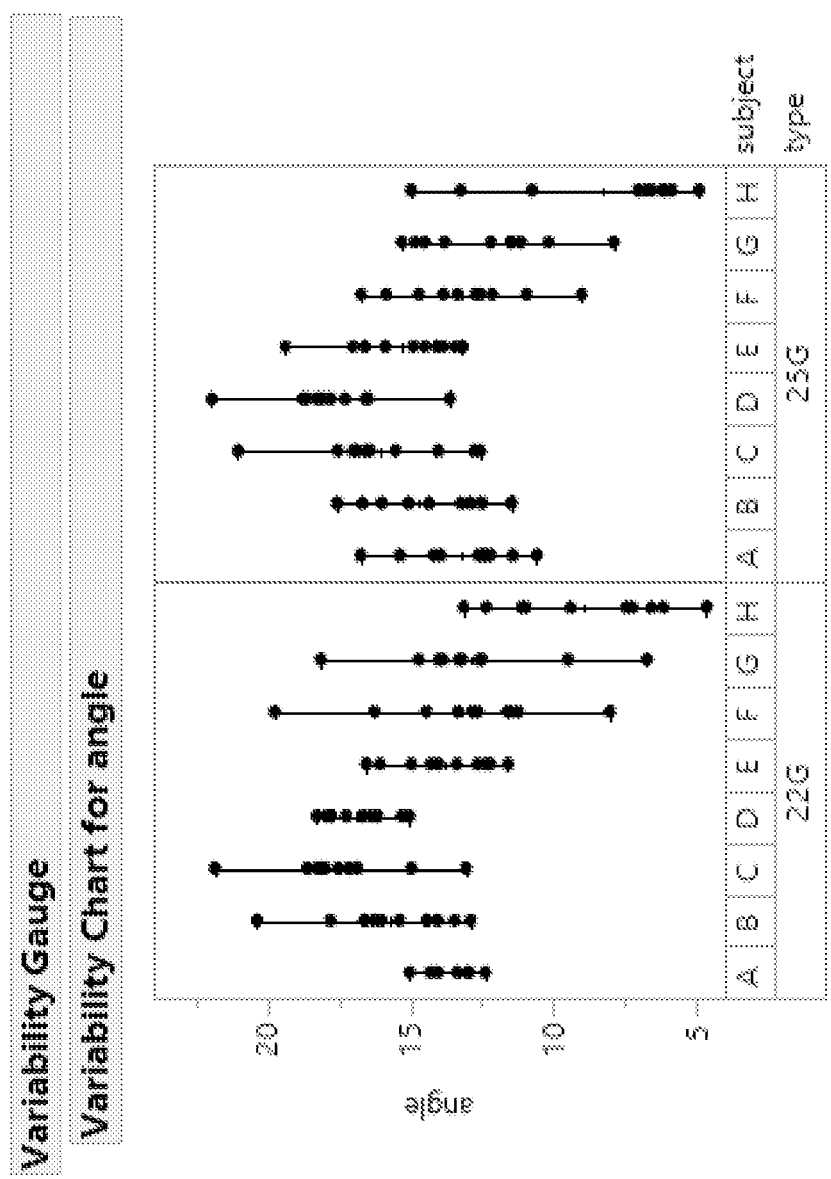
FIG. 14 shows a chart of angle of needle bend from a study performed by the inventors analyzing variability in manually bending 20 spinal needles (ten 22-gauge and ten 25-gauge per participant). The x-axis illustrates the participants (A-H) and is divided into 22-gauge and 25-gauge needle sizes. The y-axis illustrates the variability in the angle of needle bend (cm) applied to the needle tip.

FIG. 14 shows a chart of angle of needle bend from a study performed by the inventors analyzing variability in manually bending 20 spinal needles (ten 22-gauge and ten 25-gauge per participant). The x-axis illustrates the participants (A-H) and is divided into 22-gauge and 25-gauge needle sizes. The y-axis illustrates the variability in the angle of needle bend (cm) applied to the needle tip.

All patents, patent applications, provisional applications, and other publications referred to or cited herein are incorporated by reference in their entirety, including all figures and tables, to the extent they are not inconsistent with the explicit teachings of this specification.

Additionally, the entire contents of the references cited within the references cited herein are also entirely incorporated by reference.

Any reference in this specification to "one embodiment," "an embodiment," "example embodiment," "further embodiment," "alternative embodiment," etc., is for literary convenience. The implication is that any particular feature, structure, or characteristic described in connection with such an embodiment is included in at least one embodiment of the invention. The appearance of such phrases in various places in the specification does not necessarily refer to the same embodiment. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

It is to be noted that the terms "first," "second," and the like as used herein do not denote any order, quantity, or importance, but rather are used to distinguish one element from another. The terms "a" and "an" do not denote a limitation of quantity, but rather denote the presence of at least one of the referenced item. Furthermore, to the extent that the terms "including," "includes," "having," "has," "with," or variants thereof are used in either the detailed description and/or the claims, such terms are intended to be inclusive in a manner similar to the term "comprising." The modifier "about" used in connection with a quantity is inclusive of the stated value and has the meaning dictated by the context (e.g., includes the degree of error associated with measurement of the particular quantity). It is to be noted that all ranges disclosed within this specification are inclusive and are independently combinable.

REFERENCES

1. Panjeton G D, Abdul-rahim A, Reynolds P S, Antony A B. Survey of Interventional Pain Physicians on Bending Spinal Needles for Chronic Pain Procedures. Interv Pain Manag Reports [Internet]. 2020; 4(1). Available from: https://www.ipmreportsjournal.com/current/pdf?article=NDAz
2. Sitzman B T, Uncles D R. The Effects of Needle Type, Gauge, and Tip Bend on Spinal Needle Deflection. Reg Anesth Pain Med [Internet]. 1996; 82:297-301. Available from: https://journals.lww.com/anesthesiaanalgesia/Fulltext/1996/02000The_Effects_of_Needle_Type,_Gauge,_and_Tip_Bend_on.14.aspx?trendmd_shared=0

What is claimed is:

1. A needle bending apparatus, comprising:
   a housing having an aperture for receiving a shaft of a needle, the aperture comprising a longitudinal axis;
   a first and second abutment member disposed on a front side of the housing;
   at least one abutment member of the first and second abutment members comprising a needle interfacing surface for supporting a portion of the needle and providing a surface upon which the needle may be bent;
   wherein the aperture is between the first and the second abutment members and wherein the housing comprises on the front side thereof: grooves for receiving at least a portion of a needle and maintaining said portion of the needle while the needle is bent, said grooves demarcating an angle of the bend of the bent needle, the grooves comprising a first groove positioned at a 10-degree angle relative to the longitudinal axis of the aperture, said first groove for aligning with a needle to impart a 10 degree angle bend in the needle, a second groove positioned at a 15 degree angle relative to the longitudinal axis of the aperture, said second groove for aligning with a needle to impart a 15 degree angle bend in the needle, and a third groove positioned at a 20 degree angle relative to the longitudinal axis of the aperture, said third groove for aligning with a needle to impart a 20 degree angle bend in the needle.

2. The needle bending apparatus of claim 1, further comprising on the front-side of the housing at least one indicator for identifying a position along a shaft of the needle for imparting a bend upon alignment of the needle with the indicator.

3. A method for bending a needle comprising:
   positioning a needle through the aperture, and in the first, second, or third groove of an apparatus, according to claim 1, such that a shaft of the needle traverses the aperture and is placed against the needle interfacing surface; and
   applying a force on a proximal end of the needle to bend the needle around the at least one abutment member to impart a bend on the needle.

* * * * *